United States Patent [19]

Martin

[11] 4,268,502

[45] May 19, 1981

[54] COSMETIC TONIC FORMULATION

[75] Inventor: Joe O. Martin, Martinsville, Ind.

[73] Assignee: Eli Lilly and Company, Indianapolis, Ind.

[21] Appl. No.: 179,625

[22] Filed: Aug. 20, 1980

[51] Int. Cl.³ .......................................... A61K 31/745
[52] U.S. Cl. ................................ 424/83; 424/273 R; 424/358; 424/365
[58] Field of Search .................. 424/83, 358, 365, 273

[56] References Cited

U.S. PATENT DOCUMENTS

| | | | |
|---|---|---|---|
| 3,196,079 | 7/1965 | Herrold et al. | 424/83 |
| 4,164,564 | 8/1979 | Chen | 424/83 |
| 4,216,201 | 8/1980 | Calvo | 424/63 |

OTHER PUBLICATIONS

Leszczynska-Bakal et al., Dissert. Pharm. Pharmacol., 1970, vol. 22, No. 1, pp. 56-60.
A-C Polyethylene Bulletin, (5011-22-1A), 7/14/77.
A-C Polyethylene Bulletin, (5011-24-2), 8-16-77.
A-C Polyethylene Bulletin, (5189-4-4), 8/8/78.

*Primary Examiner*—Dale R. Ore
*Attorney, Agent, or Firm*—Karen B. O'Connor; Arthur R. Whale

[57] ABSTRACT

A skin tonic formulation, which is one of four components used in a cosmetic regime, is disclosed. Applying the regime to the skin increases epidermal cell turnover without skin irritation. The other three components used in the regime are a cleanser, a cream, and a lotion.

1 Claim, No Drawings

COSMETIC TONIC FORMULATION

BACKGROUND OF THE INVENTION

This invention relates to one component for use in a novel cell renewal cosmetic regime, which regime increases the rate of cell turnover without skin irritation.

In the natural renewing cycle of skin, cells are constantly being born, rising through the epidermal layers to the surface and falling off. A young skin renews its surface layers every two to three weeks. A mature skin can take twice as long. And the longer this process takes, the more cells develop areas of weakness that cause a faster loss of natural moisture and the dry lifeless appearance that's found in older looking skin.

Acceleration of natural cell renewal or turnover speeds the replacement of dead cells by new ones in the outer epidermal layer or stratum corneum, thereby giving the skin a younger-looking appearance. The newer cells are moist and fresh, replacing the old, dry cells on the surface.

Although irritation of the skin will increase the sloughing off of dead stratum corneum cells, such irritation is undesirable because of the damage to the skin. It is, therefore, desirable to increase cell turnover without irritation.

SUMMARY OF THE INVENTION

It is, therefore, an object of the present invention to provide a skin tonic formulation, which is one of four components for use in a cosmetic regime. The regime's use increases epidermal cell turnover without skin irritation. The other three components for use in the regime are: a cleanser, a cream, and a lotion.

DESCRIPTION OF THE PREFERRED EMBODIMENTS

In accordance with this invention there is provided a skin tonic formulation, which is one of four components for use in a cosmetic regime. The use of the regime increases cell turnover without causing skin irritation. The regime consists of the application to the skin of a cleanser, a cream, a lotion, and a tonic. Each of the three other components is a separate invention; the cleanser is claimed in application Ser. No. 179,628, filed of even date herewith, the cream is claimed in application Ser. No. 179,626, also filed of even date herewith, and the lotion is claimed in application Ser. No. 179,629, filed of even date herewith. The use of the four components in a regime to increase cell turnover without causing skin irritation is claimed in application Ser. No. 179,627, filed of even date herewith.

The preferred regime usually begins in the morning with the use of the tonic, followed by the lotion. Later, usually at night, the cleanser is used, and then the tonic and cream are applied. However, the order and the timing of the use of the four products can be varied to suit individual needs. For example, the cleanser also can be used in the morning. Some effect will be obtained even if all the compositions are not used or if there is a delay between usage.

The tonic formulation consists essentially of, in percent be weight:

| Ingredients | Percent |
| --- | --- |
| deionized water | 80.12 |
| polyethylene and polypropylene glycol | 2.00 |
| glyoxyldiureide | 0.20 |
| polyethylene glycol 300 | 9.00 |
| imidazolidinyl urea | 0.40 |
| denatured alcohol | 7.00 |
| methyl p-hydroxybenzoate | 0.10 |
| propyl p-hydroxybenzoate | 0.05 |
| polyoxyethylene sorbitan fatty acid ester | 0.30 |
| ethoxylated oleyl alcohol | 0.50 |
| menthol | 0.03 |
| fragrance | 0.30 |

In general, the individual ingredients used in the formulation should be of a quality or purity (such as U.S.P. or N.F.) suitable for cosmetic use.

The formulation of this invention is prepared by mixing the ingredients according to conventional methods. The preparation of this formulation is described in the following example. The example is illustrative of the formulation embraced by the invention, but is not to be construed as limiting the invention.

EXAMPLE 1

Tonic

Formulation:

| Phase | Ingredient | Percent by weight |
| --- | --- | --- |
| A | deionized water | 80.12 |
| | UCON Lubricant 75H450 (Union Carbide, polyethylene and polypropylene glycol) | 2.00 |
| | Allantoin (Sutton and Schuylkill, glyoxyldiureide) | 0.20 |
| | PEG-300 (polyethylene glycol 300) | 9.00 |
| | imidazolidinyl urea | 0.40 |
| B | SDA 40-2, 190 Proof (denatured alcohol) | 7.00 |
| | methylparaben (methyl p-hydroxy benzoate) | 0.10 |
| | propylparaben (propyl p-hydroxy benzoate) | 0.05 |
| | Polysorbate 60 (ICI, polyoxyethylene sorbitan fatty acid ester) | 0.30 |
| | POE (10) oleyl ether (ethoxylated oleyl alcohol) | 0.50 |
| | menthol | 0.03 |
| | Essence 66.001 (Firmenich, fragrance) | 0.30 |

Procedure:

The ingredients of Phase A are mixed with a Lightnin' mixer until the solution is clear. The ingredients of Phase B are then mixed in a separate container with a Lightnin' mixer until clear. Phase B is slowly added to Phase A with mixing. The product is filtered through a security type filter and is hazy after filtration. The product is then stored in a non-plastic container. All equipment and personnel should be grounded, since the formulation contains alcohol.

When the above-described formulations are used in accordance with the method of this invention, the rate of skin cell turnover is increased without skin irritation. The rate of skin cell turnover is frequently reported as transit time. Transit time is defined as the time required for a newly formed stratum corneum cell to rise up through the stratum corneum and finally slough off. Therefore, the less transit time required, the better the appearance of the skin, because younger cells are on its surface.

The test for measuring transit time is described by L. H. Jansen, et al., "Improved Fluorescence Staining Technique for Estimating Turnover of the Human Stratum Corneum," *British Journal of Dermatology*, 1974, 90, 9–12. The transit or replacement time of the human stratum corneum is determined by measuring the number of days required for a fluorescent marker, dansyl chloride, to disappear after application to the skin. The dansyl chloride only stains the stratum corneum (outer cell layer) and the shedding of the stratum corneum is signified by the disappearance of the dansyl chloride.

Using the Jansen procedure, the transit time of the present regime is measured and compared with the transit time of several commercially available, skin-care cosmetic products, identified as products A to E in Table I. Dansyl chloride is applied to both upper inner arms of each subject, after two weeks of pretreatment with the product. Then one arm is treated daily with the particular product, while the other arm is untreated. The number of days required for the dansyl chloride to disappear from each arm is then recorded. The results for the treated arms are averaged for the particular product and compared to the average for the untreated arms. The results are shown in Table I. The larger the difference between the control and treated times, the more effective is the product.

The test was run using women from young (19–29 years) and middle (31–58 years) age groups for products A–E and the regime.

The present regime consists of using all four components in the following order: the cleanser and tonic were used in the morning, followed by the lotion; later, at night, the cleanser was used and then the tonic and cream were applied.

TABLE I

| Product | Number of Subjects | Mean Transit Time$^a$ | | |
| --- | --- | --- | --- | --- |
| | | Treated with Product | Control (untreated) | Difference |
| A | 11 | 16.1 | 17.0 | 0.9 |
| B | 11 | 15.9 | 17.3 | 1.4 |
| C | 10 | 14.1 | 15.3 | 1.2 |
| D | 10 | 13.5 | 16.0 | 2.5 |
| E | 10 | 18.2 | 22.1 | 3.9 |
| Regime (young age group) | 8 | 13.75 | 20.63 | 6.88 |
| Regime (middle age group) | 12 | 15.67 | 22.08 | 6.41 |

$^a$in days

I claim:

1. A skin tonic formulation consisting essentially of, in percent by weight:

| Ingredients | Percent |
| --- | --- |
| deionized water | 80.12 |
| polyethylene and polypropylene glycol | 2.00 |
| glyoxyldiureide | 0.20 |
| polyethylene glycol (300) | 9.00 |
| imidazolidinyl urea | 0.40 |
| denatured alcohol | 7.00 |
| methyl p-hydroxybenzoate | 0.10 |
| propyl p-hydroxybenzoate | 0.05 |
| polyoxyethylene (60) sorbitan fatty acid ester | 0.30 |
| polyoxyethylene (10) oleyl ether | 0.50 |
| menthol | 0.03 |
| fragrance | 0.30 |

* * * * *